(12) United States Patent
Tanaka

(10) Patent No.: US 10,398,809 B2
(45) Date of Patent: Sep. 3, 2019

(54) SUCTION DEVICE

(71) Applicant: Murata Manufacturing Co., Ltd., Kyoto (JP)

(72) Inventor: Nobuhira Tanaka, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 236 days.

(21) Appl. No.: 15/402,733

(22) Filed: Jan. 10, 2017

(65) Prior Publication Data

US 2017/0143878 A1    May 25, 2017

Related U.S. Application Data

(63) Continuation of application No. PCT/JP2015/068748, filed on Jun. 30, 2015.

(30) Foreign Application Priority Data

Jul. 11, 2014  (JP) ................. 2014-143124

(51) Int. Cl.
| A61M 1/00 | (2006.01) |
| A61M 5/00 | (2006.01) |
| A61M 25/00 | (2006.01) |
| A61M 31/00 | (2006.01) |
| A61M 25/16 | (2006.01) |
| A61M 39/02 | (2006.01) |
| A61M 27/00 | (2006.01) |

(52) U.S. Cl.
CPC ........ *A61M 1/0031* (2013.01); *A61M 1/0066* (2013.01); *A61M 1/0086* (2014.02); *A61M 2205/3327* (2013.01); *A61M 2205/3344* (2013.01); *A61M 2205/502* (2013.01); *A61M 2205/52* (2013.01); *A61M 2210/0618* (2013.01)

(58) Field of Classification Search
CPC .......... A61M 1/00; A61M 5/00; A61M 25/00; A61M 31/00; A61M 25/16; A61M 39/02; A61M 27/00; A61K 9/02
See application file for complete search history.

(56) References Cited

U.S. PATENT DOCUMENTS

| 6,471,679 B1 | 10/2002 | Suh |
| 2010/0324510 A1 | 12/2010 | Andresen |
| 2012/0046625 A1 | 2/2012 | Johannison |

(Continued)

FOREIGN PATENT DOCUMENTS

| JP | H11-342144 A | 12/1999 |
| JP | 2000-060962 A | 2/2000 |

(Continued)

OTHER PUBLICATIONS

International Search Report issued in Application No. PCT/JP2015/068748 dated Oct. 6, 2015.

(Continued)

*Primary Examiner* — Tatyana Zalukaeva
*Assistant Examiner* — Ilya Y Treyger
(74) *Attorney, Agent, or Firm* — Pearne & Gordon LLP

(57) ABSTRACT

A suction device (10) includes a nose piece (11) that is mounted by inserting a leading end thereof into a nasal cavity, a suction pump (21) that sucks external fluid using the nose piece (11) with a suction pressure in accordance with a driving voltage, and a driving controller (31) that repeats a state of applying the driving voltage to the suction pump (21) and a state of stopping application of the driving voltage.

10 Claims, 10 Drawing Sheets

(56) References Cited

U.S. PATENT DOCUMENTS

2013/0018338 A1    1/2013  Weston et al.
2016/0271305 A1    9/2016  Kurihara

FOREIGN PATENT DOCUMENTS

| JP | 2001-218831 A | 8/2001 |
| JP | 2007-117273 A | 5/2007 |
| JP | 2010-506691 A | 3/2010 |
| JP | 2010-531200 A | 9/2010 |
| JP | 2012-525202 A | 10/2012 |
| WO | 2013/140255 A1 | 9/2013 |
| WO | 2015/115516 A1 | 8/2015 |

OTHER PUBLICATIONS

Written Opinion issued in Application No. PCT/JP2015/068748 dated Oct. 6, 2015.
Notice of Reasons for Rejection for Japanese Application No. 2016-532887, dated Mar. 20, 2018.

THICKNESS DIRECTION

LENGTHWISE DIRECTION

WIDTH DIRECTION

SUCTION DEVICE

This is a continuation of International Application No. PCT/JP2015/068748 filed on Jun. 30, 2015 which claims priority from Japanese Patent Application No. 2014-143124 filed on Jul. 11, 2014. The contents of these applications are incorporated herein by reference in their entireties.

BACKGROUND OF THE DISCLOSURE

Field of the Disclosure

The present disclosure relates to a suction device that is used for removing nasal mucus, phlegm, and the like.

Description of the Related Art

Cold, rhinitis, empyema, and the like excessively increase secretion of nasal mucus to cause symptoms of nasal congestion and the like. In general, a patient can clear the nasal congestion by blowing his/her nose by himself/herself. However, for an infant or the like who cannot blow his/her nose by himself/herself, a caregiver needs to remove the nasal mucus thereof. In this case, the caregiver can remove a small amount of the nasal mucus using a tissue or a cotton swab but it is difficult to remove a large amount of the nasal mucus.

In recent years, an electric suction device capable of easily removing a large amount of the nasal mucus has spread (for example, see Patent Document 1). For example, the suction device (see Patent Document 1) includes a vacuum generation unit, a nasal mucus storage cylinder, a suction port, and an operation unit. The vacuum generation unit and the nasal mucus storage cylinder are coupled to each other with a pipe line. The nasal mucus storage cylinder is coupled to the suction port for sucking nasal mucus. The operation unit switches suction and suction stop of the nasal mucus. With the suction device, when the suction port is inserted into a nasal cavity and a button of the operation unit is pressed, the nasal mucus is sucked from the suction port in a vacuum state generated by the vacuum generation unit and the nasal mucus is accumulated in the nasal mucus storage cylinder. When the button of the operation unit is released, the vacuum state is cancelled and suction is interrupted.

Patent Document 1: Japanese Unexamined Patent Application Publication No. 2001-218831

BRIEF SUMMARY OF THE DISCLOSURE

For a newborn or the like incapable of explaining the generation of the nasal congestion or the like by himself/herself, a caregiver needs to regularly observe a symptom of a patient and perform suction of nasal mucus when the nasal congestion or the like is generated even in a sleep time period. Therefore, the caregiver cannot continuously get sleep and bears a great burden.

If the suction device is continuously operated, the burden on the caregiver can be largely reduced. In this case, however, the operation sound of the suction device is continuously generated or the patient cannot smoothly breath, resulting in increase in a feeling of discomfort of the patient. Furthermore, operation time becomes long to cause operation failure, increase the power consumption of the suction device, and so on.

To address the above-described problems, if the generation of the nasal congestion or the nasal mucus can be detected and notified to the caregiver, or the nasal mucus can be automatically sucked, it is very useful for the caregiver and the patient. In order to detect the generation of the nasal mucus, a member such as a liquid sensor needs to be additionally provided in the suction device and a mechanism for mounting the sensor on an affected part is required. This causes the configuration of the suction device to be complicated and increases time and effort for mounting.

An object of the present disclosure is to provide a suction device capable of automatically sucking nasal mucus and the like with a simple configuration without increasing time and effort.

A suction device according to an aspect of the present disclosure includes a suction unit, a suction pump, and a driving controller. The suction unit is mounted on an affected part. The suction pump sucks external fluid using the suction unit with a suction pressure in accordance with a driving voltage. The driving controller repeats a state of applying the driving voltage to the suction pump and a state of stopping application of the driving voltage.

With this configuration, when the suction device is intermittently operated in a state in which the suction unit is mounted on the affected part, the suction device regularly repeats a state of sucking the external fluid and a state of stopping the suction. Therefore, a caregiver is not required to observe a symptom of a patient and perform a suction operation. Furthermore, when the suction device is intermittently operated, the power consumption and the operation time can be suppressed. In addition, a feeling of discomfort of the patient due to the operation sound of the suction device and suction can be reduced. For example, breathing of the patient is unlikely be interfered by matching the intermittent operation to a breathing interval of the patient, thereby largely suppressing the feeling of discomfort of the patient. In the case where the nasal mucus is generated at an interval of several ten minutes to several hours, by adjusting the suction device to be intermittently operated at the similar time interval, time and frequency at which the patient experiences the feeling of discomfort can be reduced while the nasal mucus is appropriately sucked.

Furthermore, it is preferable that the suction device include a detection unit which detects a suction state in the suction unit, and the driving controller adjust the driving voltage based on the suction state in the suction unit, which has been detected by the detection unit.

With this configuration, a pattern of the suction pressure of the suction pump can be optimized by automatically adjusting the driving voltage based on the suction state in the suction unit. The optimization of the driving voltage can reduce the power consumption and reduce the feeling of discomfort that the patient experiences due to the operation sound of the suction device and the suction. For example, the absence or presence of the nasal mucus is detected and the driving voltage is increased when the nasal mucus is present. With this, the nasal mucus can be removed reliably when the nasal mucus is present while the suction pump is operated with a minimum necessary driving voltage (initial voltage) in a normal state to prevent the nasal cavities from being damaged and the patient from being experienced a strong feeling of discomfort. Furthermore, the viscosity of the external fluid that is sucked by the suction unit is detected and the driving voltage is increased when the viscosity is high. With this, even the nasal mucus having high viscosity can be removed reliably while the suction of the fluid at an excessively high suction pressure and flow rate is prevented when the viscosity of the nasal mucus is low to prevent the nasal cavities from being damaged and the patient from being experienced the strong feeling of discomfort.

Furthermore, it is preferable that the detection unit detect a state of the suction pump and detect the suction state in the suction unit based on the detected state of the suction pump. In particular, it is preferable that the suction device further include a storage unit which previously stores a correspondence relation between the suction state in the suction unit and the state of the suction pump and the detection unit detect the suction state in the suction unit with reference to the storage unit. With this configuration, a member functioning as a detection unit needs not to be additionally provided in the suction unit, thereby simplifying the suction unit and the connection configuration thereof.

In addition, it is preferable that the suction pump have a piezoelectric element operating upon reception of application of the driving voltage. With this configuration, a frequency of the driving voltage of the piezoelectric element can be made to deviate from frequencies of audible sound, thereby reducing the operation sound in comparison with a driving source such as a motor.

Moreover, it is preferable that the detection unit detect a state of an impedance of the piezoelectric element as the state of the suction pump. The state of the impedance of the piezoelectric element varies in accordance with the suction pressure of the suction pump. Accordingly, the suction state in the suction unit can be detected based on the state of the impedance of the piezoelectric element. With this configuration, the suction state in the suction unit can be detected without additionally adding the member such as the pressure sensor.

It is preferable that the detection unit detect an amplitude of an electric current flowing through the piezoelectric element as the state of the impedance of the piezoelectric element. The magnitude of the impedance of the piezoelectric element varies in accordance with the suction pressure in the suction unit. The magnitude of the impedance of the piezoelectric element can be calculated as an amplitude ratio between the current flowing through the piezoelectric element and the driving voltage of the piezoelectric element. Accordingly, when the amplitude of the driving voltage of the piezoelectric element is known, the suction state in the suction unit can be detected based on the amplitude of the current flowing through the piezoelectric element. Furthermore, the amplitude of the current can be detected with a small-sized and simple circuit, thereby providing the detection unit easily.

Furthermore, it is preferable that the detection unit detect a phase difference between a current flowing through the piezoelectric element and the driving voltage of the piezoelectric element as the state of the impedance of the piezoelectric element. The phase difference between the current flowing through the piezoelectric element and the driving voltage thereof varies in accordance with the suction state in the suction unit. Therefore, the suction state in the suction unit can be detected based on the phase difference between the current flowing through the piezoelectric element and the driving voltage thereof. Detection based on the phase difference enables the suction state in the suction unit to be grasped with high accuracy even under conditions that the driving voltage or a temperature fluctuates.

Moreover, it is preferable that the detection unit detect a resonant frequency of the piezoelectric element as the state of the impedance of the piezoelectric element, and the driving controller drive the piezoelectric element at the resonant frequency. The resonant frequency of the piezoelectric element varies in accordance with the suction state in the suction unit. Therefore, the suction state in the suction unit can be detected based on the resonant frequency of the piezoelectric element. In addition, vibration of the piezoelectric element can be maximized by matching a driving frequency of the suction pump with the resonant frequency of the piezoelectric element, thereby suppressing electric power necessary for a desired suction pressure.

In addition, it is preferable that the suction device further include a notification unit which notifies of the state detected by the detection unit. With this configuration, the notification unit is used to notify a caregiver of a state of a patient, thereby enabling the caregiver to grasp the generation of an abnormal event, and the like, while suppressing increase in time and effort for observing the patient. As the notification unit, a liquid crystal display unit, a display lamp, a wireless communication unit, or the like can be used.

According to the present disclosure, nasal mucus and the like can be automatically sucked with a simple configuration without increasing time and effort and complicating operation procedures.

Figure 3A:
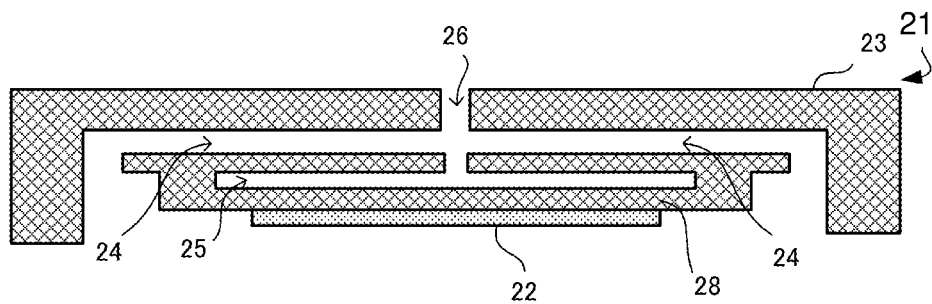
Figure 3B:
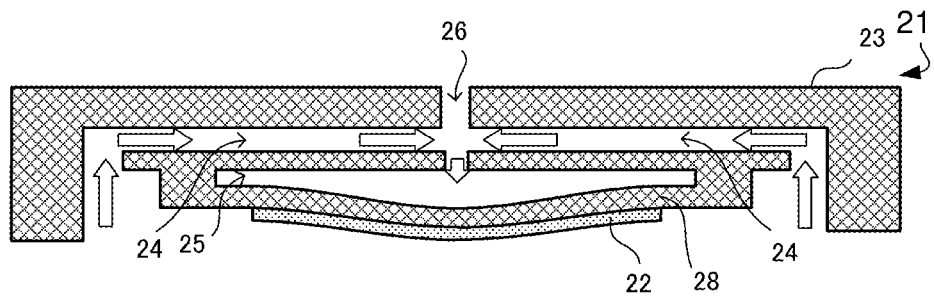
Figure 3C:
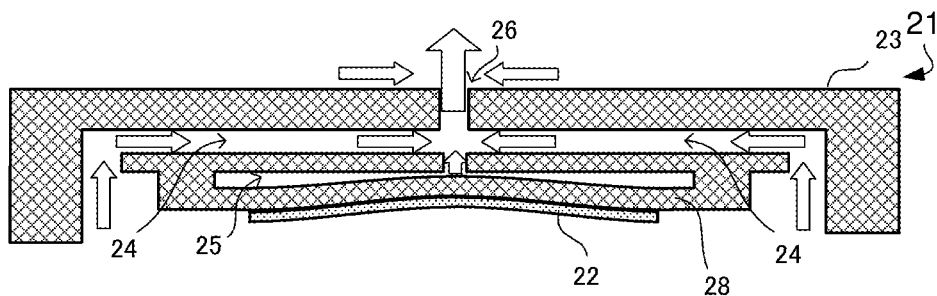

Each of FIGS. 3A, 3B and 3C is a schematic view illustrating a vibration mode of the suction pump in the first embodiment.

Figure 4:
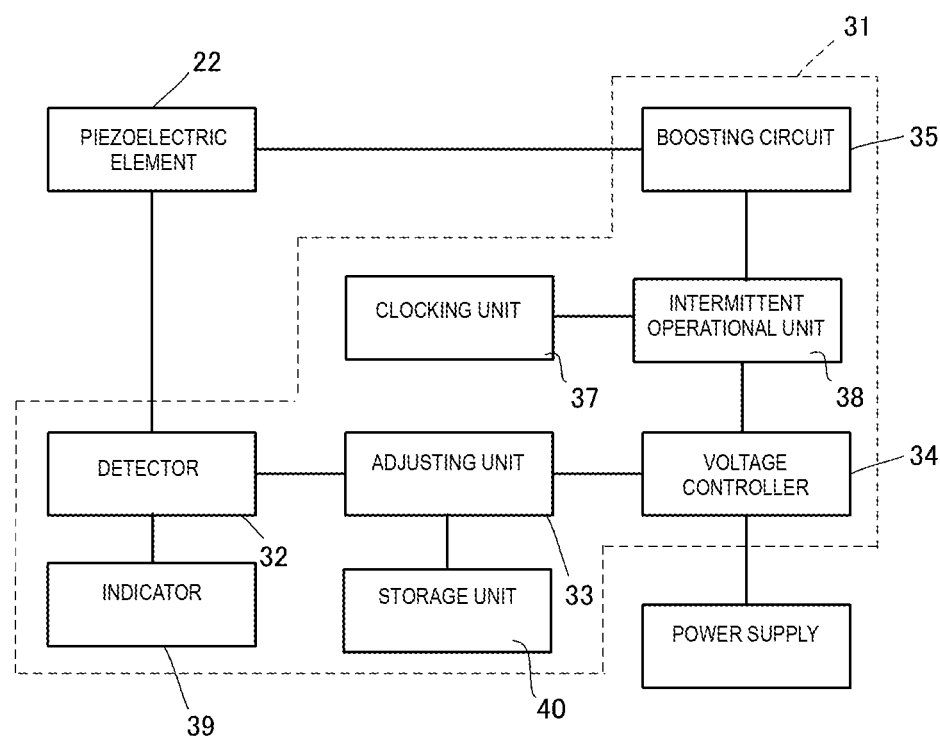

FIG. 4 is a block diagram of a driving controller in the first embodiment.

Figure 5A:
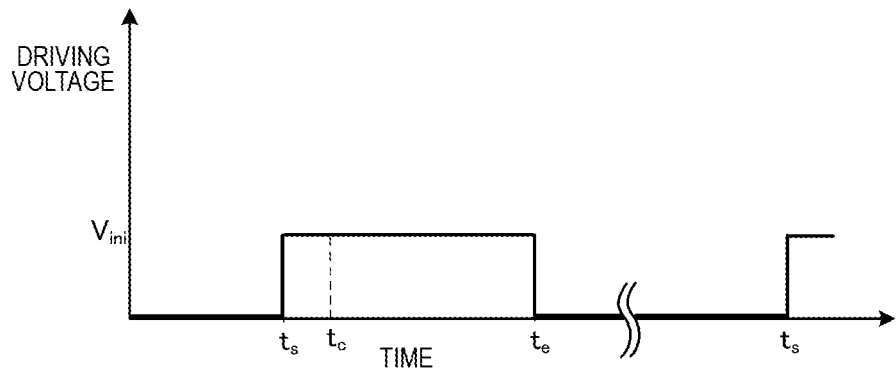
Figure 5B:
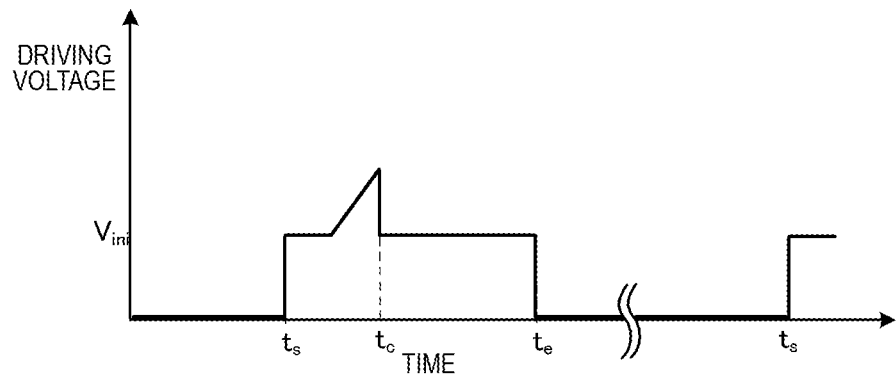
Figure 5C:
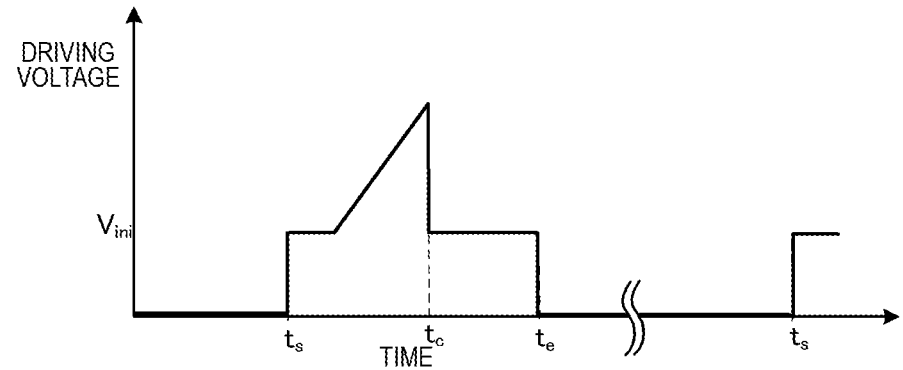

Each of FIGS. 5A, 5B and 5C is a graph illustrating an amplitude pattern of a driving voltage that is applied to a piezoelectric element in the first embodiment.

Figure 6:
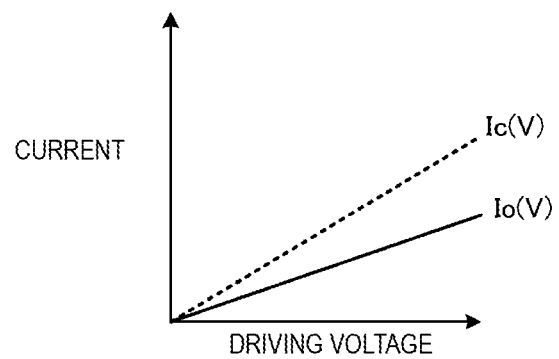

FIG. 6 is a graph illustrating a correspondence relation between an amplitude of the driving voltage that is applied to the piezoelectric element and a current flowing through the piezoelectric element in the first embodiment.

Figure 7:
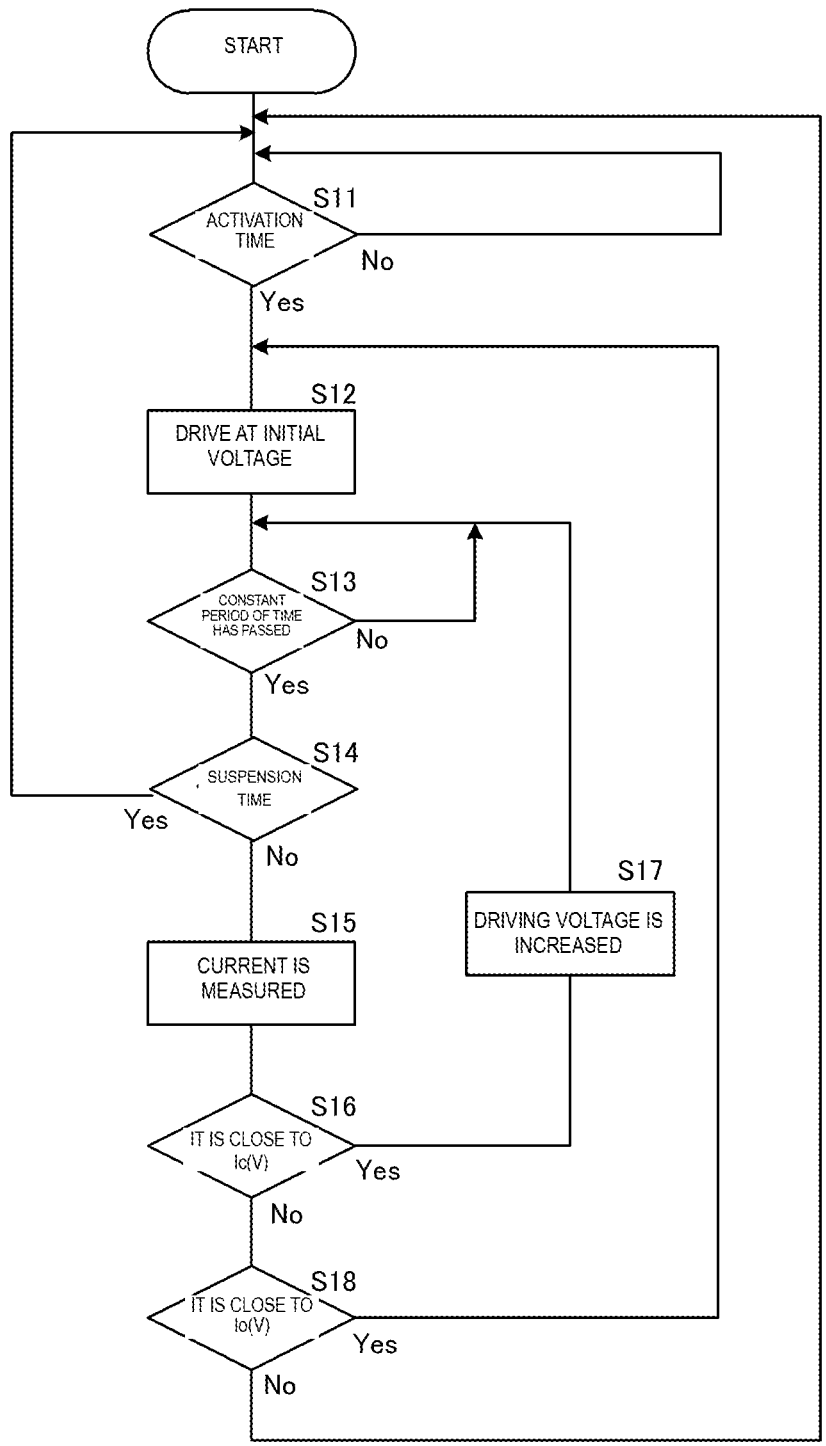

FIG. 7 is a flowchart illustrating the operations of the driving controller in the first embodiment.

Figure 8:
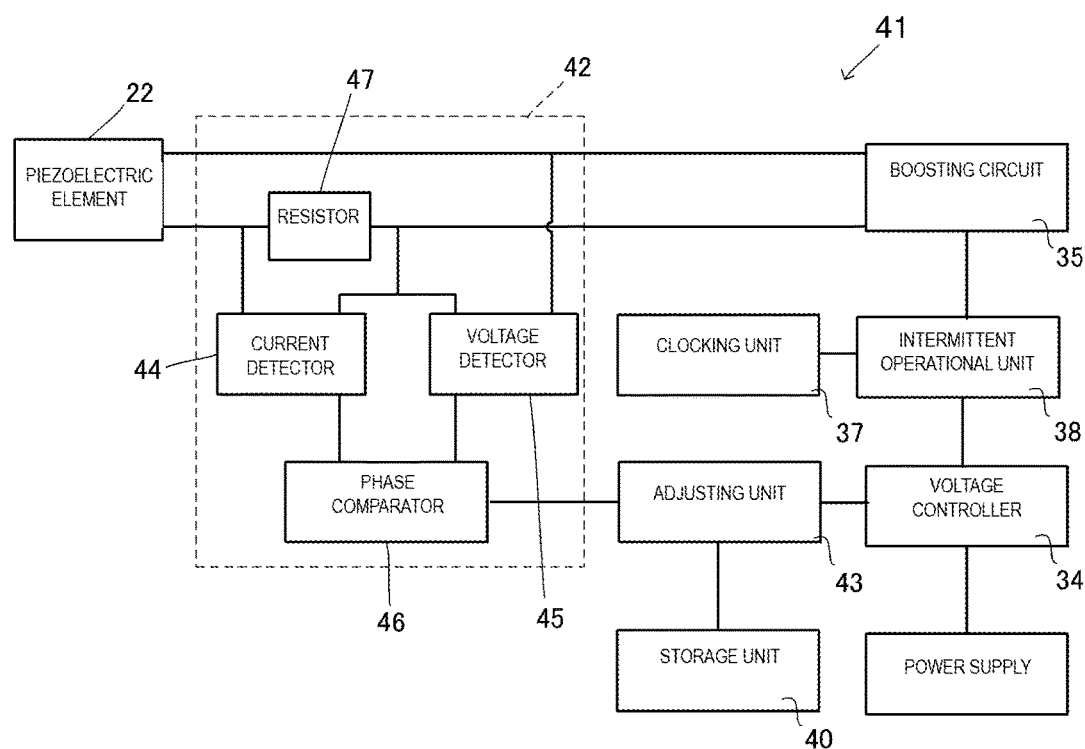

FIG. 8 is a block diagram of a driving controller according to a second embodiment.

Figure 9:
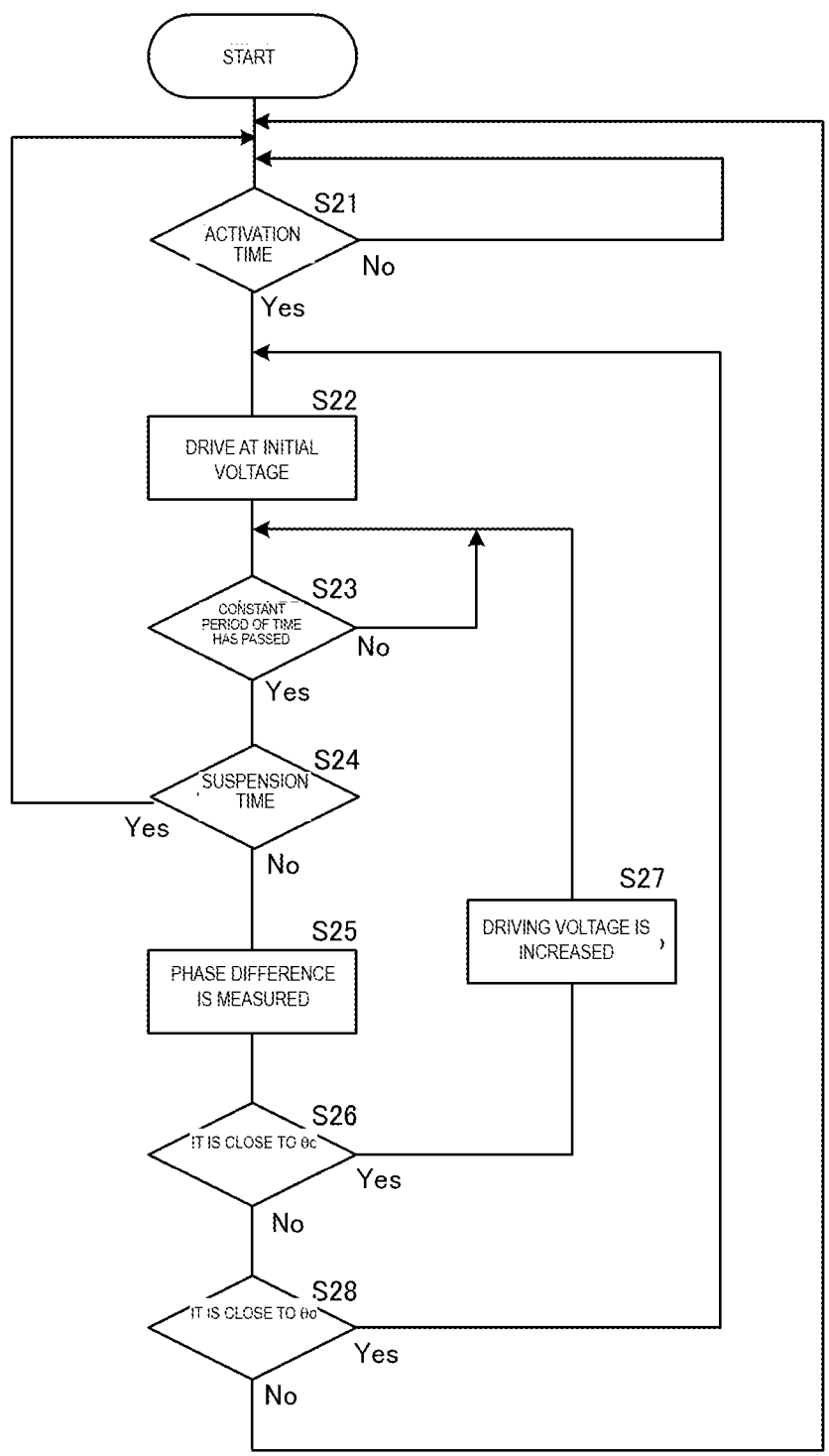

FIG. 9 is a flowchart illustrating the operations of the driving controller in the second embodiment.

Figure 10:
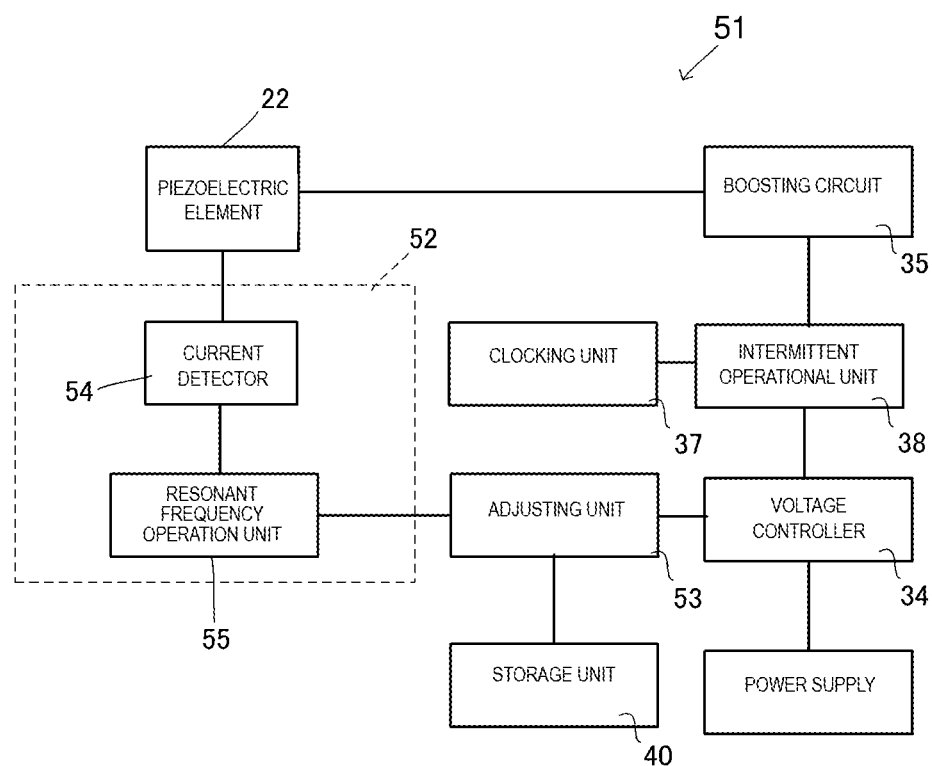

FIG. 10 is a block diagram of a driving controller according to a third embodiment.

Figure 11:
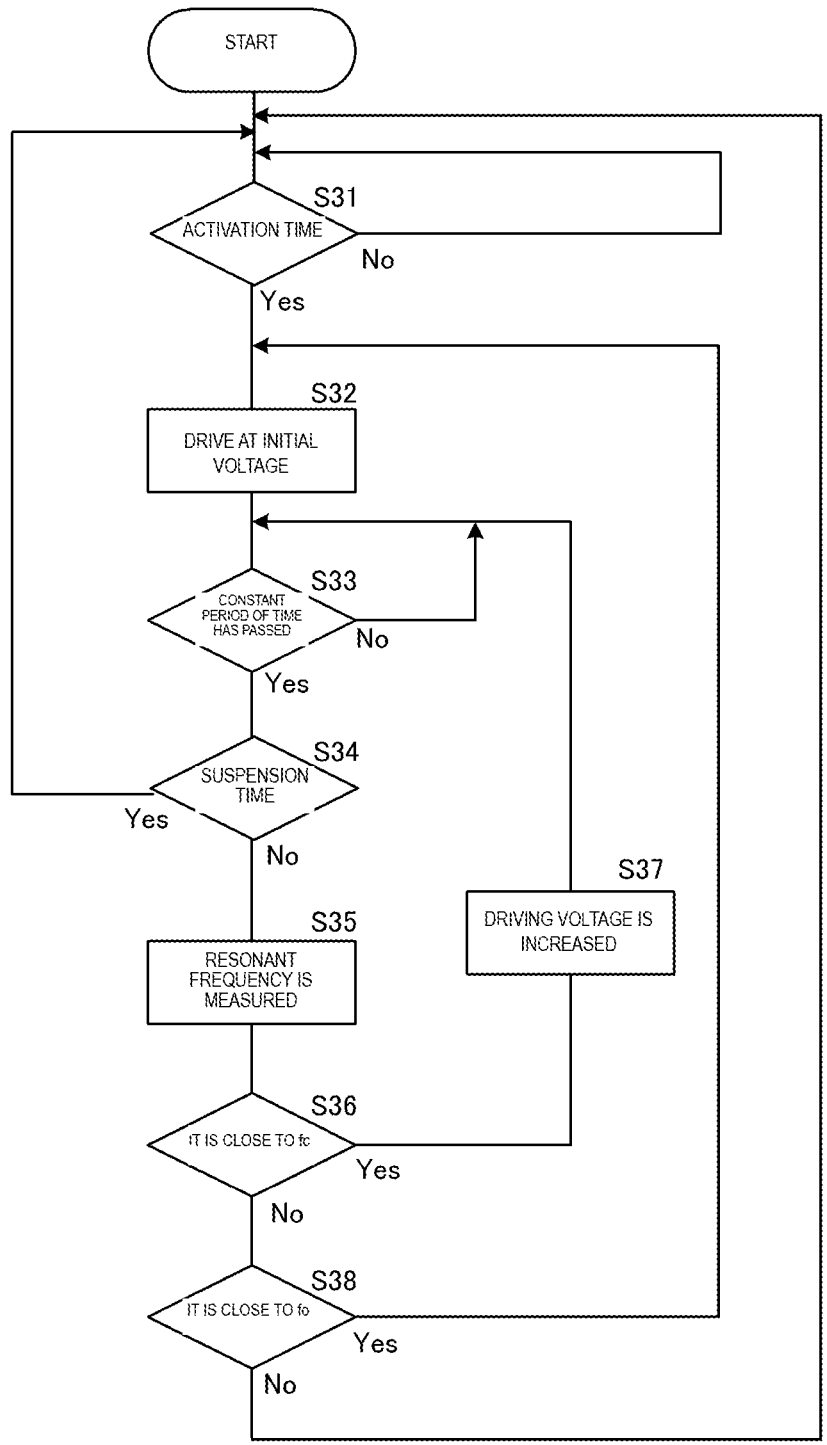

FIG. 11 is a flowchart illustrating the operations of the driving controller in the third embodiment.

DETAILED DESCRIPTION OF THE DISCLOSURE

《First Embodiment》

Hereinafter, a suction device 10 according to a first embodiment of the present disclosure will be described.

Figure 1:
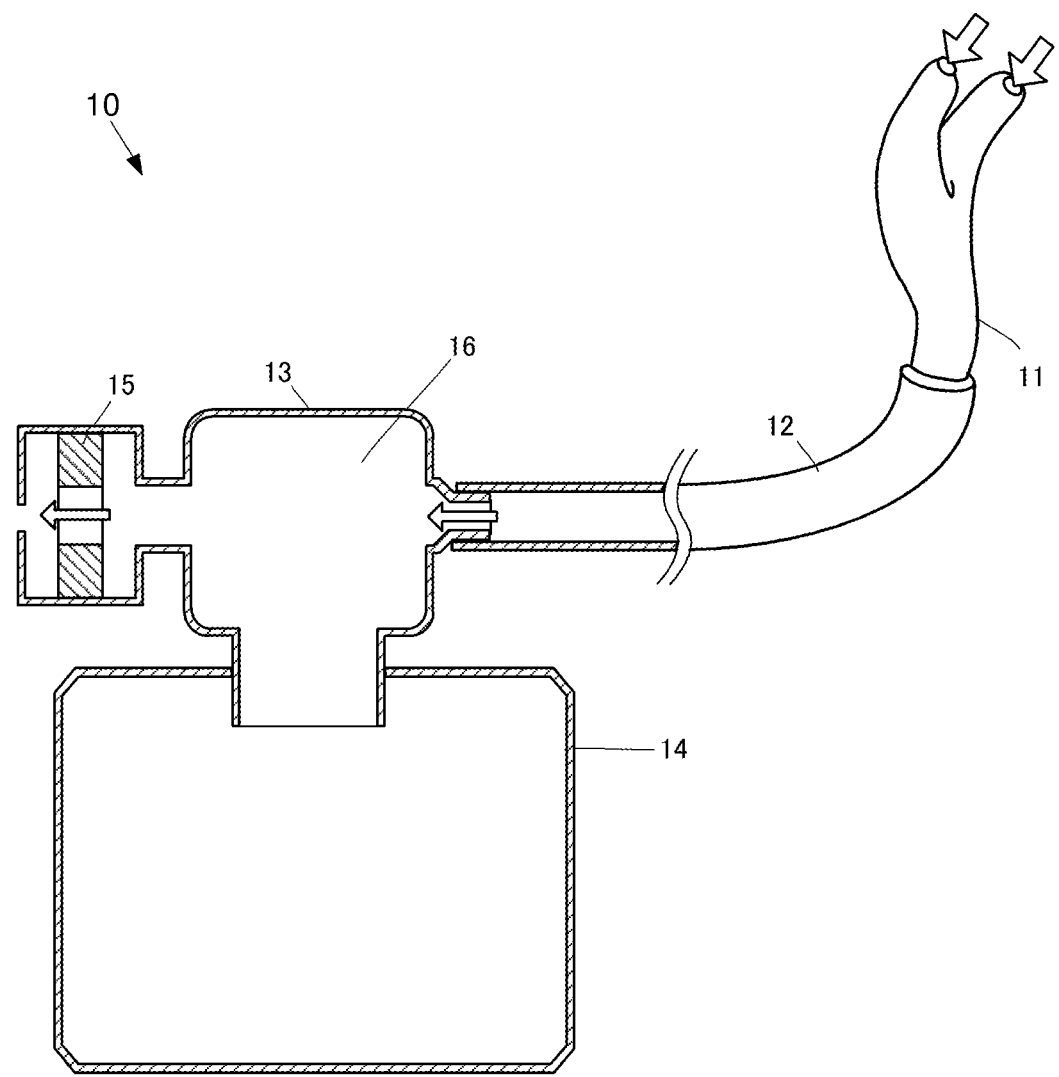
FIG. 1 is a schematic cross-sectional view of a suction device according to a first embodiment.

FIG. 1 is a schematic cross-sectional view of the suction device 10. The suction device 10 includes a nose piece 11, a connection tube 12, a separator 13, a storing unit 14, and a piezoelectric driving unit 15. The nose piece 11 corresponds to a suction unit according to the present disclosure and is mounted on an affected part such as the nasal cavities of an infant in a state in which the leading ends thereof are inserted thereinto. The connection tube 12 has flexibility and connects the nose piece 11 and the separator 13. The separator 13 has a container shape that is opened to the lower side. The storing unit 14 has a container shape that is opened to the upper side and is provided under the separator 13. Although not illustrated in FIG. 1, an indicator 39 (see FIG. 4) displaying a state of the leading ends of the nose piece 11 is provided in the suction device 10. Furthermore, a suction pump 21 (see FIG. 2) and a driving controller 31 (see FIG. 4) are provided in the piezoelectric driving unit 15.

The nose piece 11, the connection tube 12, the separator 13, and the piezoelectric driving unit 15 are connected in this order in a state of being aligned from the front side to the rear side in the suction device 10. The nose piece 11, the connection tube 12, the separator 13, the storing unit 14, and the piezoelectric driving unit 15 are provided with a flow path 16 communicating from the leading ends of the nose piece 11 to the rear end of the piezoelectric driving unit 15.

When the piezoelectric driving unit 15 is driven, the flow of the fluid toward the rear end of the piezoelectric driving unit 15 from the leading ends of the nose piece 11 is generated in the flow path 16. The nose piece 11 sucks nasal mucus in the nasal cavities together with the air. The separator 13 isolates the nasal mucus from the fluid that is sucked from the connection tube 12 and causes the nasal mucus to drop downward. The storing unit 14 stores therein the nasal mucus that drops from the separator 13.

Figure 2:
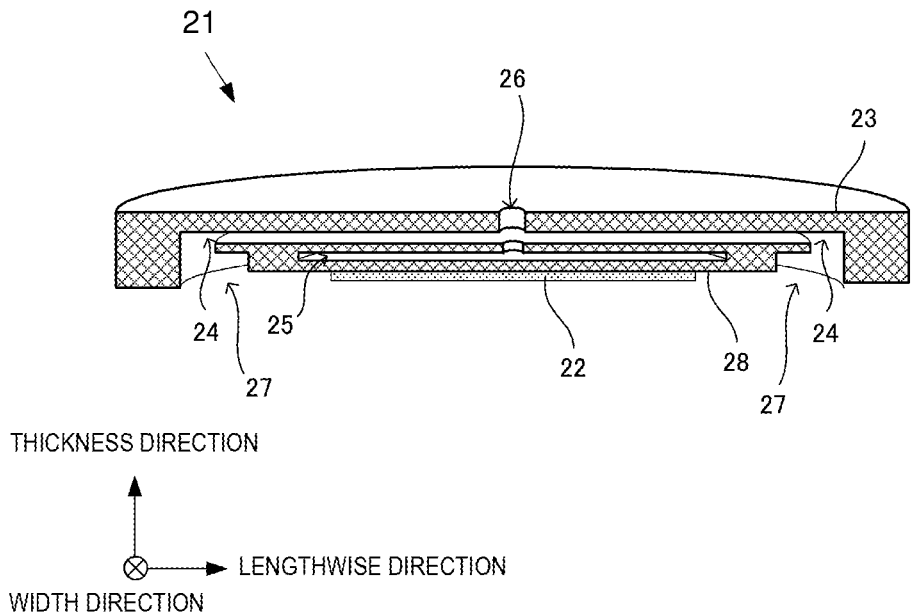
FIG. 2 is a cross-sectional view of a suction pump in the first embodiment.

FIG. 2 is a cross-sectional view of the suction pump 21. The suction pump 21 includes a piezoelectric element 22 and a structure 23. The structure 23 has a schematic outer shape of a circular plate that is thin in the thickness direction. A discharge port 26 is opened in the vicinity of the center in the top surface of the structure 23. A suction port 27 is opened in the vicinity of the edge of the bottom surface of the structure 23. The suction pump 21 is arranged such that the suction port 27 side faces the separator 13 side.

A flow path 24 and a pump chamber 25 are provided in the structure 23. The flow path 24 communicates with the discharge port 26 on the top surface of the structure 23, extends to the outer circumference sides from the vicinity of the center in the structure 23, and communicates with the suction port 27 on the bottom surface of the structure 23. The pump chamber 25 is a thin cylindrical space that is provided at the bottom surface side of a communication portion of the discharge port 26 and the flow path 24 and is opened to the communication portion of the discharge port 26 and the flow path 24.

The inner bottom surface of the pump chamber 25 in the structure 23 is configured as a diaphragm (vibration plate) 28 capable of vibrating in a bending manner. The diaphragm 28 has a circular plate shape and the top surface thereof faces the pump chamber 25. The top surface of the diaphragm 28 opposes the discharge port 26 with the pump chamber 25 interposed therebetween. The piezoelectric element 22 has a circular plate shape that is thin in the thickness direction and is bonded to the bottom surface of the diaphragm 28. The piezoelectric element 22 has piezoelectricity that it tends to extend and contract in an in-plane direction of the main surface thereof upon reception of application of an alternating-current (AC) driving voltage.

Each of FIGS. 3A, 3B and 3C is a schematic view illustrating a vibration mode of the suction pump 21. The piezoelectric element 22 and the diaphragm 28 are bonded to each other to configure a unimorph structure and are displaced in the thickness direction by driving the piezoelectric element 22. To be specific, when the piezoelectric element 22 tends to extend from a still state as illustrated in FIG. 3A, the diaphragm 28 bends in a projecting manner to the piezoelectric element 22 side (bottom surface side) and the volume of the pump chamber 25 is increased, as illustrated in FIG. 3B. With this, a negative pressure is generated in the pump chamber 25, the negative pressure is transmitted to the flow path 24 communicating with the pump chamber 25, and the fluid in the flow path 24 is sucked into the pump chamber 25.

When the piezoelectric element 22 tends to contract from the still state as illustrated in FIG. 3A, the diaphragm 28 bends in a projecting manner to the pump chamber 25 side (top surface side) and the volume of the pump chamber 25 is decreased, as illustrated in FIG. 3C,. With this, the fluid in the pump chamber 25 is discharged to the outside from the discharge port 26 and the fluid in the flow path 24 is drawn by the flow of the fluid to be discharged from the discharge port 26 because the pump chamber 25 and the discharge port 26 oppose each other with the flow path 24 interposed therebetween.

With the above-described bending vibration of the piezoelectric element 22 and the diaphragm 28, in the suction pump 21, periodical volume fluctuation and pressure fluctuation are repeatedly generated in the pump chamber 25 and inertia force acts on air flow. This causes air flow with which the fluid in the flow path 24 is discharged from the discharge port 26 to be constantly generated. In the suction pump 21, the diaphragm 28 opposes the discharge port 26 with the flow path 24 and the pump chamber 25 interposed therebetween. Therefore, the fluid efficiency of the suction pump 21 is high to realize a high suction pressure and low power consumption simultaneously.

FIG. 4 is a block diagram illustrating an example of the configuration of the driving controller 31.

The driving controller 31 herein has a function of intermittently operating the piezoelectric element 22 and a function of detecting a state of the leading ends of the nose piece 11 and controlling the driving voltage of the piezoelectric element 22 to be optimum. In the present disclosure, it is sufficient that the driving controller 31 has at least the function of intermittently operating the piezoelectric element 22 and the function of controlling the driving voltage of the piezoelectric element 22 to be optimum is not essential.

The driving controller 31 includes a detector 32, an adjusting unit 33, a storage unit 40, a voltage controller 34, a boosting circuit 35, the indicator 39, a clocking unit 37, and an intermittent operational unit 38. The detector 32 configures a detection unit according to the present disclosure.

The voltage controller 34 controls a power supply voltage and supplies it to the boosting circuit 35 with the intermittent operational unit 38 interposed therebetween. The clocking unit 37 measures the current time. The intermittent operational unit 38 outputs the voltage to the boosting circuit 35 for a predetermined activation period of time every time a defined suspension period of time has passed based on the current time measured by the clocking unit 37. The boosting circuit 35 boosts the power supply voltage to generate a driving voltage and applies the driving voltage to the piezoelectric element 22. With this, the piezoelectric element 22 is driven in the activation period of time and causes the suction device 10 to suck the nasal mucus and the like. Furthermore, the driving of the piezoelectric element 22 is stopped in the suspension period of time and causes the suction device 10 to stop to suck the nasal mucus and the like.

A frequency of the driving voltage of the piezoelectric element 22 deviates from a frequency band of audible sound. Therefore, the driving sound of the piezoelectric element 22 is smaller than that of a motor and the like. The piezoelectric element 22 has a property that the impedance thereof is influenced by a state (a suction pressure and a flow rate) of the fluid flowing through the flow path 24 illustrated in FIG. 2. Accordingly, when a correspondence relation between the state of the fluid flowing through the flow path 24 and the influence on the impedance of the piezoelectric element 22 is known, the state of the fluid flowing through the flow path 24 can be grasped based on the impedance of the piezoelectric element 22. Furthermore, the state of the fluid flowing through the flow path 24 is influenced by the state of the leading ends of the nose piece 11. Accordingly, when a correspondence relation between the state of the leading ends of the nose piece 11 and the influence on the impedance of the piezoelectric element 22 is known, the state of the leading ends of the nose piece 11 can be grasped based on the state of the impedance of the piezoelectric element 22.

The detector 32 detects the state of the impedance of the piezoelectric element 22. The storage unit 40 previously stores therein the correspondence relation between the state of the impedance of the piezoelectric element 22 and the suction pressure or the state of the leading ends of the nose piece 11 as a table or an operation expression. The detector 32 grasps the suction pressure and the state of the leading ends of the nose piece 11 based on the detected state of the impedance of the piezoelectric element 22 by referring to the storage unit 40. The adjusting unit 33 sets the voltage controller 34 so as to provide an optimum driving voltage pattern in accordance with the state of the leading ends of the nose piece 11 based on the detection result of the detector 32 and the voltage controller 34 causes the boosting circuit 35 to output a voltage with the intermittent operational unit 38 interposed therebetween. The voltage controller 34 changes the output voltage or controls a boosting ratio of the boosting circuit 35 so as to control the driving voltage that is outputted from the boosting circuit 35. The indicator 39 has a function of displaying information of the detection result of the detector 32 on a liquid crystal display unit, a display lamp, or the like, and a function of transmitting it to the outside using a communication line. When the indicator 39 transmits the information to the outside using the communication line, a user can grasp the degree of the nasal congestion of the infant or the like to grasp the deterioration, improvement, or the like of a lesion by causing an external apparatus to determine and display the degree of the nasal congestion in time series.

It should be noted that some of the functions of the adjusting unit 33, the voltage controller 34, the intermittent operational unit 38, and the detector 32 can be implemented by a single microcomputer, for example. For example, when a microcomputer that performs PWM control is used, an I/O terminal of the microcomputer is connected to the detector 32 and a PWM output terminal of the microcomputer is directly connected to the boosting circuit 35. The driving voltage that is outputted from the boosting circuit 35 can be controlled by changing a duty ratio of the PWM control output by the microcomputer.

Each of FIGS. 5A, 5B and 5C is a conceptual view illustrating an optimum amplitude pattern of the driving voltage in accordance with the state of the leading ends of the nose piece 11. It should be noted that the amplitude pattern of the driving voltage is equivalent to a variation pattern of the suction pressure in the leading ends of the noise piece 11.

FIG. 5A is a graph illustrating the optimum amplitude pattern of the driving voltage when nasal mucus having low viscosity is present in the nasal cavities or when no nasal mucus is present in the nasal cavities. FIG. 5B is a graph illustrating the optimum amplitude pattern of the driving voltage when nasal mucus having intermediate viscosity is present in the nasal cavities. FIG. 5C is a graph illustrating the optimum amplitude pattern of the driving voltage when nasal mucus having high viscosity is present in the nasal cavities. Time ts indicates activation time at which a nasal mucus suction operation is started. Time tc indicates the time at which the nasal mucus in the nasal cavities has been sucked and the nasal mucus becomes absent in the nasal cavities. Time te indicates the suspension time at which the nasal mucus suction operation is suspended. In this example, the time taken for the voltage adjustment and the current measurement is not considered.

First, the case in which the leading ends of the nose piece 11 suck the nasal mucus having low viscosity will be described. As illustrated in FIG. 5A, no driving voltage is applied to the piezoelectric element 22 and the suction device 10 is suspended before the activation time ts. At the activation time ts, a driving voltage having an initial amplitude Vini is applied to the piezoelectric element 22, and a relatively low suction pressure is generated in the leading ends of the nose piece 11 to start the suction of the nasal mucus having low viscosity. In a period to the time tc from the activation time ts, the driving voltage is not changed from the initial amplitude Vini and the leading ends of the nose piece 11 suck the nasal mucus having low viscosity while the relatively low suction pressure in the leading ends of the nose piece 11 is kept. Also in a period to the suspension time te from the time tc at which the suction of the nasal mucus in the nasal cavities is completed, the driving voltage is not changed from the initial amplitude Vini and the leading ends of the nose piece 11 suck the air in the nasal cavities while the relatively low suction pressure in the leading ends of the nose piece 11 is kept. At the suspension time te, the application of the driving voltage to the piezoelectric element 22 is stopped and the suction device 10 is suspended again. Thereafter, the suspension period of time lasts to the next activation time ts, and then, the suction device 10 is activated again at the next activation time ts.

As described above, the suction device 10 is intermittently operated. Therefore, when the nose piece 11 is left in a state of being mounted on the affected part, the state in which the leading ends of the nose piece 11 suck the nasal mucus in the nasal cavities and the state in which they stop suction are repeated regularly. Accordingly, usage of the suction device 10 eliminates the necessity of regular observation of the symptom of the patient and the suction operation by the caregiver. Furthermore, the suction device 10 is intermittently operated and the power consumption and operation time are thereby suppressed. Moreover, the feeling of discomfort that the patient experiences due to the operation sound of the suction device 10 and the suction can be reduced.

Next, the case in which the leading ends of the nose piece 11 suck the nasal mucus having intermediate viscosity will be described. As illustrated in FIG. 5B, no driving voltage is applied to the piezoelectric element 22 and the suction device 10 is suspended before the activation time ts. At the activation time ts, the driving voltage having the initial amplitude Vini is applied to the piezoelectric element 22, and a relatively low suction pressure is generated in the leading ends of the nose piece 11. In this case, the leading ends of the nose piece 11 cannot suck much nasal mucus having intermediate viscosity with the low suction pressure. Then, the change in the state of the leading ends of the nose piece 11 causes the predetermined change in the impedance of the piezoelectric element 22.

The change in the impedance of the piezoelectric element 22 is detected and the amplitude of the driving voltage of the piezoelectric element 22 is set to be larger than the initial amplitude Vini. With this, in the period to the time tc from the activation time ts, the driving voltage is gradually increased from the initial amplitude Vini and the suction pressure in the leading ends of the nose piece 11 is gradually higher, so that the leading ends of the nose piece 11 become capable of sucking the nasal mucus having intermediate viscosity.

When the leading ends of the nose piece 11 completes the suction of the nasal mucus having intermediate viscosity at the time tc and the leading ends of the nose piece 11 are then made into states of sucking the air in the nasal cavities and the nasal mucus having lower viscosity, the change in the state of the leading ends of the nose piece 11 causes the predetermined change in the impedance of the piezoelectric element 22.

Then, the change in the impedance of the piezoelectric element 22 is detected and the amplitude of the driving voltage of the piezoelectric element 22 is returned to the initial amplitude Vini. With this, in the period to the suspension time te from the time tc at which suction of the nasal mucus having intermediate viscosity is completed, the driving voltage is not changed from the initial amplitude Vini and the leading ends of the nose piece 11 continuously suck the air in the nasal cavities and the nasal mucus having low viscosity while the relatively low suction pressure in the leading ends of the nose piece 11 is kept. At the suspension time te, the application of the driving voltage to the piezoelectric element 22 is stopped and the suction device 10 is suspended again. Thereafter, the suspension period of time lasts to the next activation time ts, and then, the suction device 10 is activated again at the next activation time ts.

As described above, the suction device 10 not only is intermittently operated but also adjusts the driving voltage so as to provide the optimum amplitude pattern in accordance with the state of the leading ends of the nose piece 11 and optimizes the suction pressure in the leading ends of the nose piece 11. Therefore, the power consumption of the suction device 10 and the feeling of discomfort that the patient experiences due to the operation sound of the suction device 10 and the suction can be reduced. To be more specific, the suction pressure is increased when the suction device 10 sucks the nasal mucus having intermediate viscosity from the nasal cavities, thereby sucking the nasal mucus having intermediate viscosity in the nasal cavities more reliably. Furthermore, the suction pressure is lowered after the suction of the nasal mucus having intermediate viscosity from the nasal cavities is completed, thereby preventing the nasal cavities from being damaged due to an excessively high suction pressure and flow rate and the patient from being experienced the strong feeling of discomfort.

Next, the case in which the leading ends of the nose piece 11 suck the nasal mucus having high viscosity will be described. As illustrated in FIG. 5C, no driving voltage is applied to the piezoelectric element 22 and the suction device 10 is suspended before the activation time ts. At the activation time ts, the driving voltage having the initial amplitude Vini is applied to the piezoelectric element 22, and a relatively low suction pressure is generated in the leading ends of the nose piece 11. In this case, the leading ends of the nose piece 11 cannot suck much nasal mucus having high viscosity with the low suction pressure. Then, the change in the state of the leading ends of the nose piece 11 causes the predetermined change in the impedance of the piezoelectric element 22.

The change in the impedance of the piezoelectric element 22 is detected and the amplitude of the driving voltage is set to be larger than the initial amplitude Vini. With this, in the period to the time tc from the activation time ts, the driving voltage is gradually increased from the initial amplitude Vini and the suction pressure in the leading ends of the nose piece 11 is gradually higher, so that the leading ends of the nose piece 11 become capable of sucking the nasal mucus having high viscosity.

When the leading ends of the nose piece 11 completes the suction of the nasal mucus having high viscosity at the time tc, the leading ends of the nose piece 11 are then made into states of sucking the air in the nasal cavities and the nasal mucus having lower viscosity. The change in the state of the leading ends of the nose piece 11 causes the predetermined change in the impedance of the piezoelectric element 22.

Then, the change in the impedance of the piezoelectric element 22 is detected and the adjusting unit 33 returns the amplitude of the driving voltage to the initial amplitude Vini. With this, in the period to the suspension time te from the time tc at which the suction of the nasal mucus in the nasal cavities is completed, the driving voltage is not changed from the initial amplitude Vini and the leading ends of the nose piece 11 continuously suck the air in the nasal cavities while the relatively low suction pressure in the leading ends of the nose piece 11 is kept. At the suspension time te, the application of the driving voltage to the piezoelectric element 22 is stopped and the suction device 10 is suspended again. Thereafter, the suspension period of time lasts to the next activation time ts, and then, the suction device 10 is activated again at the next activation time ts.

As described above, also when the viscosity of the nasal mucus in the nasal cavities is higher, the suction device 10 increases the driving voltage for a longer period of time until the suction pressure in accordance with the viscosity is provided. Accordingly, the suction device 10 can suck the nasal mucus in the nasal cavities reliably regardless of the viscosity of the nasal mucus. With the pattern of the driving voltage described herein, the nasal mucus is continuously sucked with the driving voltage having the initial amplitude after the suction of the nasal mucus having intermediate viscosity or high viscosity is completed, as an example. Alternatively, the output of the driving voltage may be stopped after the suction of the nasal mucus having intermediate viscosity or high viscosity is completed.

Next, the function of detecting the state of the leading ends of the nose piece 11 will be described more in detail.

The magnitude of the impedance of the piezoelectric element 22 is influenced by the state of the leading ends of the nose piece 11. Furthermore, the magnitude of the impedance of the piezoelectric element 22 can be expressed as a ratio between the amplitude of the current flowing through the piezoelectric element 22 and the amplitude of the driving voltage that is applied to the piezoelectric element 22. Accordingly, when a correspondence relation among the state of the leading ends of the nose piece 11, an amplitude value of the current flowing through the piezoelectric element 22, and an amplitude value of the driving voltage that is applied to the piezoelectric element 22 is known, the state of the leading ends of the nose piece 11 can also be grasped by detecting the amplitude value of the current by the detector 32 and grasping the output voltage of the boosting circuit 35.

FIG. 6 is a graph illustrating the correspondence relation between the amplitude of the driving voltage that is applied to the piezoelectric element 22 and the amplitude of the current flowing through the piezoelectric element 22. FIG. 6 illustrates an amplitude Ic(V) of the current when the leading ends of the nose piece 11 are completely closed and an amplitude Io(V) of the current when the leading ends of the nose piece 11 are completely opened.

Inclination with respect to change in the driving voltage is different between the amplitude Ic(V) of the current when the leading ends of the nose piece 11 are completely closed and the amplitude Io(V) of the current when the leading ends of the nose piece 11 are completely opened. The amplitude Ic(V) of the current when the leading ends of the nose piece 11 are completely closed is basically larger than the amplitude Io(V) of the current when the leading ends of the nose piece 11 are completely opened.

Accordingly, when the amplitude I of the actual current, which is measured by the detector 32, is closer to the amplitude Ic(V) of the current relative to the amplitude Io(V) of the current described above, there is high possibility that the current state is close to the state in which the leading ends of the nose piece 11 are closed and it is difficult to suck the nasal mucus. On the other hand, when the amplitude I of the actual current, which is measured by the detector 32, is closer to the amplitude Io(V) of the current relative to the amplitude Ic(V) of the current described above, there is high possibility that the current state is close to the state in which the leading ends of the nose piece 11 are opened and it is easy to suck the nasal mucus.

FIG. 7 is a flowchart illustrating an example of the operations of the driving controller 31 when the driving controller 31 detects the above-described change in the current flowing through the piezoelectric element 22 and controls the driving voltage of the piezoelectric element 22 to be optimum.

The driving controller 31 determines whether the current time which is measured by the clocking unit 37 is the activation time after a predetermined period of time (for example, 1 hour) has passed from the previous suspension time in a suspension state in which no driving voltage is applied to the piezoelectric element 22 (S11). When the current time is the activation time (Yes at S11), the driving controller 31 applies a driving voltage defined as a minimum voltage to the piezoelectric element 22 using the intermittent operational unit 38 and the boosting circuit 35 (S12). With this, the piezoelectric element 22 is driven and the suction device 10 starts the nasal mucus suction operation using the nose piece 11.

Then, after a constant period of time (for example, approximately 1 second) has passed (Yes at S13), the driving controller 31 determines whether the current time which is measured by the clocking unit 37 is the suspension time after a predetermined period of time (for example, 20 seconds) has passed from the previous activation time (S14). When the current time is not the suspension time (No at S14), the driving controller 31 measures, by the detector 32, a current I flowing through the piezoelectric element 22 (S15).

Subsequently, the driving controller 31 determines, by the adjusting unit 33, whether the amplitude I of the actual current, which is measured by the detector 32, is closer to the current amplitude Io(V) corresponding to the output voltage V of the boosting circuit 35 at this time or to the current amplitude Ic(V) so as to grasp the state of the leading ends of the nose piece 11. For example, an operation expression or a table of a threshold value corresponding to an intermediate value between the current amplitude Io(V) and the current amplitude Ic(V) is stored in the storage unit and the driving controller 31 compares, by the adjusting unit 33, the amplitude I of the actual current, which is measured by the detector 32, and the threshold value. When the measured amplitude I of the actual current is closer to the current amplitude Ic(V) (Yes at S16), the driving controller 31 determines, by the adjusting unit 33, that the leading ends of the nose piece 11 cannot sufficiently suck the nasal mucus and applies a driving voltage changed to have an amplitude larger than an original amplitude to the piezoelectric element 22 using the voltage controller 34 and the boosting circuit 35 (S17). When the amplitude of the driving voltage is increased and exceeds a limit value, the amplitude of the driving voltage is kept to be the original amplitude. Then, the determination whether the current time is the suspension time (S14) and the measurement of the current (S15) are repeated after the constant period of time (for example, approximately 1 second) has passed (Yes at S13) again. With this, the suction pressure in the leading ends of the nose piece 11 is gradually increased until the nasal mucus can be removed, thereby removing even the nasal mucus having high viscosity reliably.

On the other hand, when the measured amplitude I of the actual current is closer to the previously grasped amplitude Io(V) of the current in the opened state (No at S16 and Yes at S18), the driving controller 31 determines, by the adjusting unit 33, that the leading ends of the nose piece 11 have succeeded to suck the nasal mucus or the leading ends of nozzles do not hit the nasal mucus in the nasal cavities and applies a driving voltage changed to have the initial amplitude to the piezoelectric element 22 using the voltage controller 34 and the boosting circuit 35 again (S11).

The driving controller 31 repeats the above-described operation flow until it is determined that the current time which is measured by the clocking unit 37 is the suspension time (No at S14) and stops the operation till the next activation time from the suspension time (S11).

The amplitude V of the output voltage from the boosting circuit 35 is controlled by the voltage controller 34 and the like, and it is therefore preferably acquired by being read from a control value of the voltage controller 34 and the like or measuring an actual voltage value. Furthermore, the above-described operation values and table can be acquired by digital processing using a central processing device and a storage unit, or can also be realized by an analog circuit having functions corresponding to the above-described operation expression and table.

As described above, when the current flowing through the piezoelectric element 22 is detected and the driving voltage of the piezoelectric element 22 is controlled to be optimum, it is sufficient that the detector 32 has the function of detecting the current and the circuit configuration can be made extremely simple and reduced in size.

«Second Embodiment»

Next, a suction device according to a second embodiment of the present disclosure is described.

The suction device in the second embodiment of the present disclosure is different from that in the first embodiment in the configuration of a detector detecting a state of the leading ends of the nose piece 11 and functions of an adjusting unit.

FIG. 8 is a block diagram of a driving controller 41 included in the suction device in the second embodiment.

The driving controller 41 herein has a function of intermittently operating the piezoelectric element 22 and a function of detecting the state of the leading ends of the nose piece 11 based on a phase difference between a current and a voltage in the piezoelectric element 22 and controlling a driving voltage of the piezoelectric element 22 to be optimum.

The driving controller 41 includes a detector 42, an adjusting unit 43, the storage unit 40, the voltage controller 34, the boosting circuit 35, the clocking unit 37, and the intermittent operational unit 38. The detector 42 configures the detection unit according to the present disclosure and includes a current detector 44, a voltage detector 45, a phase comparator 46, and a resistor 47. The current detector 44 measures the current flowing through the piezoelectric element 22 by measuring a voltage of both ends of the resistor 47 resistance value of which is known. The resistor 47 is inserted in a voltage line connecting the piezoelectric element 22 and the boosting circuit 35. The voltage detector 45 measures a driving voltage that is applied to the piezoelectric element 22. The phase comparator 46 outputs a phase difference $\theta$ between the current measured by the current detector 44 and the voltage measured by the voltage detector 45. The adjusting unit 43 sets the voltage controller 34 so as to provide an optimum driving voltage pattern in accordance with the state of the leading ends of the nose piece 11 based on the phase difference $\theta$ output from the phase comparator 46 and causes the boosting circuit 35 to output a voltage from the voltage controller 34 with the intermittent operational unit 38 interposed therebetween.

It should be noted that, as the phase comparator 46, for example, a digital comparator of a circuit system, such as a phase frequency comparator that is used in a phase locked loop (PLL) or the like, can be used. Furthermore, some of the functions of the adjusting unit 43, the voltage controller 34, the intermittent operational unit 38, and the detector 42 can be implemented by a microcomputer, for example. For example, when a microcomputer that performs PWM control is used, an I/O terminal of the microcomputer is connected to the detector 42 and a PWM output terminal of the microcomputer is directly connected to the boosting circuit 35. The amplitude of the driving voltage that is outputted from the boosting circuit 35 can be controlled by changing a duty ratio of the PWM control output by the microcomputer.

The phase difference between the current flowing through the piezoelectric element 22 and the driving voltage thereof is different between the state in which the leading ends of the nose piece 11 are closed and the state in which the leading ends of the nose piece 11 are opened. Accordingly, when a correspondence relation between the state of the leading ends of the nose piece 11 and the phase difference between the current and the voltage in the piezoelectric element 22 is known, the state of the leading ends of the nose piece 11 can be grasped by detecting the phase of the current and the phase of the voltage by the detector 42.

A phase difference in the state in which the leading ends of the nose piece 11 are completely closed is assumed to be a phase difference $\theta c$ and a phase difference in the state in which the leading ends of the nose piece 11 are completely opened is assumed to be a phase difference $\theta o$. Under the assumption, when the actual phase difference $\theta$ which is measured by the detector 42 is closer to the phase difference $\theta c$ relative to the phase difference $\theta o$ described above, there is high possibility that the current state is close to the state in which the leading ends of the nose piece 11 are closed and it is difficult to suck the nasal mucus. On the other hand, when the actual phase difference $\theta$ which is measured by the detector 42 is closer to the phase difference $\theta o$ relative to the phase difference $\theta c$ described above, there is high possibility that the current state is close to the state in which the leading ends of the nose piece 11 are opened and it is easy to suck the nasal mucus.

FIG. 9 is a flowchart illustrating an example of operations of the driving controller 41 when the driving controller 41 detects the above-described phase difference between the current flowing through the piezoelectric element 22 and the driving voltage thereof and controls the driving voltage of the piezoelectric element 22 to be optimum.

The driving controller 41 determines whether the current time which is measured by the clocking unit 37 is the activation time after a predetermined period of time (for example, 1 hour) has passed from the previous suspension time in a suspension state in which no driving voltage is applied to the piezoelectric element 22 (S21). When the current time is the activation time (Yes at S21), the driving controller 41 applies a driving voltage defined as a minimum voltage to the piezoelectric element 22 using the intermittent operational unit 38 and the boosting circuit 35 (S22). With this, the piezoelectric element 22 is driven and the nasal mucus suction operation using the nose piece 11 is started.

Then, after a constant period of time (for example, approximately 1 second) has passed (Yes at S23), the driving controller 41 determines whether the current time which is measured by the clocking unit 37 is the suspension time after a predetermined period of time (for example, 20 seconds) has passed from the previous activation time (S24). When the current time is not the suspension time (No at S24), the driving controller 41 measures, by the detector 42, the phase difference between the current flowing through the piezoelectric element 22 and the driving voltage thereof (S25).

Subsequently, the driving controller 41 determines, by the adjusting unit 43, whether the actual phase difference $\theta$ measured by the detector 42 is closer to the known phase difference $\theta o$ or the known phase difference $\theta c$ to grasp the state of the leading ends of the nose piece 11. For example, an operation expression or a table of a threshold value corresponding to an intermediate value between the phase difference $\theta o$ and the phase difference $\theta c$ is stored in the storage unit and compares, by the adjusting unit 43, the actual phase difference $\theta$ which is measured by the detector 42 and the threshold value. When the measured actual phase difference $\theta$ is closer to the known phase difference $\theta c$ (Yes at S26), the driving controller 41 determines, by the adjusting unit 43, that the leading ends of the nose piece 11 cannot sufficiently suck the nasal mucus and applies a driving voltage changed to have an amplitude larger than an original amplitude to the piezoelectric element 22 using the voltage controller 34 and the boosting circuit 35 (S27). Then, the determination whether the current time is the suspension time (S24) and the measurement of the phase difference $\theta$ (S25) are repeated after the constant period of time (for example, approximately 1 second) has passed (Yes at S23) again. With this, the suction pressure in the leading ends of the nose piece 11 is gradually increased until the nasal mucus can be removed, thereby removing even the nasal mucus having high viscosity reliably.

On the other hand, when the measured actual phase difference $\theta$ is closer to the previously grasped phase difference $\theta o$ in the opened state (No at S26 and Yes at S28), the driving controller 41 determines, by the adjusting unit 43, that the leading ends of the nose piece 11 have succeeded to suck the nasal mucus or the leading ends of nozzles do not hit the nasal mucus in the nasal cavities and applies a driving voltage changed to have the initial amplitude to the piezoelectric element 22 using the voltage controller 34 and the boosting circuit 35 again (S21).

The driving controller 41 repeats the above-described operation flow until it is determined that the current time which is measured by the clocking unit 37 is the suspension time (No at S24) and stops the operation till the next activation time from the suspension time (S21).

It should be noted that the above-described operation values and table can be acquired by digital processing using a central processing device and a storage unit, or can also be realized by an analog circuit having functions corresponding to the above-described operation expression and table.

As described above, when the phase difference between the current flowing through the piezoelectric element 22 and the driving voltage thereof is detected and the driving voltage of the piezoelectric element 22 is controlled to be optimum, the state of the leading ends of the nose piece 11 can be grasped with high accuracy based on the phase difference θ measured by the detector 42 and the suction pressure can be adjusted with high accuracy even under conditions that the driving voltage or a temperature fluctuates.

«Third Embodiment»

Next, a suction device according to a third embodiment of the present disclosure is described.

The suction device in the third embodiment of the present disclosure is different from those in the first embodiment and the second embodiment in the configuration of a detector detecting a state of the leading ends of the nose piece 11 and functions of an adjusting unit.

FIG. 10 is a block diagram of a driving controller 51 included in the suction device in the third embodiment.

The driving controller 51 herein has a function of intermittently operating the piezoelectric element 22 and a function of detecting a state of the leading ends of the nose piece 11 based on a resonant frequency of the piezoelectric element 22 and controlling a driving voltage of the piezoelectric element 22 to be optimum.

The driving controller 51 includes a detector 52, an adjusting unit 53, the storage unit 40, the voltage controller 34, the boosting circuit 35, the clocking unit 37, and the intermittent operational unit 38. The detector 52 configures the detection unit according to the present disclosure and includes a current detector 54 and a resonant frequency operation unit 55. The current detector 54 measures a current flowing through the piezoelectric element 22. The resonant frequency operation unit 55 calculates a resonant frequency f of the piezoelectric element 22 based on the current measured by the current detector 54. The adjusting unit 53 grasps the state of the leading ends of the nose piece 11 based on the resonant frequency f calculated by the resonant frequency operation unit 55.

It should be noted that the adjusting unit 53, the voltage controller 34, the intermittent operational unit 38, and the resonant frequency operation unit 55 can be implemented by a microcomputer, for example. For example, when a microcomputer that performs PWM control is used, an I/O terminal of the microcomputer is connected to the current detector 54 and a PWM output terminal of the microcomputer is directly connected to the boosting circuit 35. The driving voltage that is outputted from the boosting circuit 35 can be controlled by changing a duty ratio of the PWM control output by the microcomputer.

The resonant frequency of the piezoelectric element 22 is a frequency at which the magnitude of the impedance of the piezoelectric element 22 is minimum, that is, a frequency at which an amplitude of the current flowing through the piezoelectric element 22 is maximum. The resonant frequency operation unit 55 causes the frequency of the driving voltage that is outputted from the boosting circuit 35 to vary in a predetermined range using the voltage controller 34, measures the current flowing through the piezoelectric element 22 at respective frequencies, and selects a frequency at which the amplitude of the measured current is maximum to calculate the resonant frequency of the piezoelectric element 22.

The resonant frequency of the piezoelectric element 22 is different between the state in which the leading ends of the nose piece 11 are closed and the state in which the leading ends of the nose piece 11 are opened. Accordingly, when a correspondence relation between the state of the leading ends of the nose piece 11 and the resonant frequency of the piezoelectric element 22 is known, the state of the leading ends of the nose piece 11 can be grasped by detecting the resonant frequency by the detector 52.

A resonant frequency of the piezoelectric element 22 in the state in which the leading ends of the nose piece 11 are completely closed is assumed to be a resonant frequency fc and a resonant frequency of the piezoelectric element 22 in the state in which the leading ends of the nose piece 11 are completely opened is assumed to be a resonant frequency fo. Under the assumption, when the actual resonant frequency f of the piezoelectric element 22, which is measured by the detector 52, is closer to the resonant frequency fc relative to the resonant frequency fo described above, there is high possibility that the current state is close to the state in which the leading ends of the nose piece 11 are closed and it is difficult to suck the nasal mucus. On the other hand, when the actual resonant frequency f which is measured by the detector 52 is closer to the resonant frequency fo relative to the resonant frequency resonant fc described above, there is high possibility that the current state is close to the state in which the leading ends of the nose piece 11 are opened and it is easy to suck the nasal mucus.

FIG. 11 is a flowchart illustrating an example of operations of the driving controller 51 when the driving controller 51 detects the above-described resonant frequency of the piezoelectric element 22 and controls the driving voltage of the piezoelectric element 22 to be optimum.

The driving controller 51 determines whether the current time which is measured by the clocking unit 37 is the activation time after a predetermined period of time (for example, 1 hour) has passed from the previous suspension time in a suspension state in which no driving voltage is applied to the piezoelectric element 22 (S31). When the current time is the activation time (Yes at S31), the driving controller 51 applies a driving voltage defined as a minimum voltage to the piezoelectric element 22 using the intermittent operational unit 38 and the boosting circuit 35 (S32). With this, the piezoelectric element 22 is driven and the nasal mucus suction operation using the nose piece 11 is started.

Then, after a constant period of time (for example, approximately 1 second) has passed (Yes at S33), the driving controller 51 determines whether the current time which is measured by the clocking unit 37 is the suspension time after a predetermined period of time (for example, 20 seconds) has passed from the previous activation time (S34). When the current time is not the suspension time (No at S34), the driving controller 51 measures, by the current detector 54 of the detector 52, the current flowing through the piezoelectric element 22 and measures, by the resonant frequency operation unit 55, the resonant frequency of the piezoelectric element 22 based on the measured current (S35). Although the description of the detail flow is omitted here, the resonant frequency operation unit 55 causes the frequency of the driving voltage that is output from the boosting circuit 35 to vary in the predetermined range using the voltage controller 34, measures the current flowing through the piezoelectric element 22 at respective frequencies, and selects the frequency at which the amplitude of the measured current is maximum to calculate the resonant frequency of the piezoelectric element 22, as described above.

Subsequently, the driving controller 51 determines, by the adjusting unit 53, whether the actual resonant frequency f measured by the detector 52 is closer to the known resonant frequency fo or the known resonant frequency fc to grasp the state of the leading ends of the nose piece 11. For example, an operation expression or a table of a threshold value corresponding to an intermediate value between the resonant frequency fo and the resonant frequency fc is stored in the storage unit and compares, by the adjusting unit 53, the actual resonant frequency f measured by the detector 52 and the threshold value. When the measured actual resonant frequency f is closer to the known resonant frequency fc (Yes at S36), the driving controller 51 determines, by the adjusting unit 53, that the leading ends of the nose piece 11 cannot sufficiently suck the nasal mucus and applies a driving voltage changed to have an amplitude larger than an original amplitude to the piezoelectric element 22 using the voltage controller 34 and the boosting circuit 35 (S37). Then, the determination whether the current time is the suspension time (S34) and the measurement of the resonant frequency f (S35) are repeated after the constant period of time (for example, approximately 1 second) has passed (Yes at S33) again. With this, the suction pressure in the leading ends of the nose piece 11 is gradually increased until the nasal mucus can be removed, thereby removing even the nasal mucus having high viscosity reliably.

On the other hand, when the measured actual resonant frequency f is closer to the previously grasped resonant frequency fo in the opened state (No at S36 and Yes at S38), the driving controller 51 determines, by the adjusting unit 53, that the leading ends of the nose piece 11 have succeeded to suck the nasal mucus or the leading ends of nozzles do not hit the nasal mucus in the nasal cavities and applies a driving voltage changed to have the initial amplitude to the piezoelectric element 22 using the voltage controller 34 and the boosting circuit 35 again (S31).

The driving controller 51 repeats the above-described operation flow until it is determined that the current time which is measured by the clocking unit 37 is the suspension time (No at S34) and stops the operation till the next activation time (S31).

It should be noted that the above-described operation values and table can be acquired by digital processing using a central processing device and a storage unit, or can also be realized by an analog circuit having functions corresponding to the above-described operation expression and table.

As described above, when the resonant frequency of the piezoelectric element 22 is detected and the driving voltage of the piezoelectric element 22 is controlled to be optimum, vibration of the piezoelectric element 22 can be increased without changing the amplitude of the driving voltage by matching the frequency of the driving voltage to the resonant frequency f measured by the detector 52. With this, higher suction pressure can be obtained even with the power consumption that is the same as those in other embodiments and the power consumption can be further reduced even with the suction pressure that is the same as those in other embodiments.

Although the suction device in each of the above-described embodiments is applied to the nasal mucus suction device, the suction device in the present disclosure is not limited to the nasal mucus suction device and may suck body fluid such as saliva and phlegm.

10 SUCTION DEVICE
11 NOSE PIECE
12 CONNECTION TUBE
13 SEPARATOR
14 STORING UNIT
15 PIEZOELECTRIC DRIVING UNIT
16 FLOW PATH
21 SUCTION PUMP
22 PIEZOELECTRIC ELEMENT
23 STRUCTURE
24 FLOW PATH
25 PUMP CHAMBER
26 DISCHARGE PORT
27 SUCTION PORT
28 DIAPHRAGM
31, 41, 51 DRIVING CONTROLLER
32, 42, 52 DETECTOR
33, 43, 53 ADJUSTING UNIT
34 VOLTAGE CONTROLLER
35 BOOSTING CIRCUIT
37 CLOCKING UNIT
38 INTERMITTENT OPERATIONAL UNIT
39 INDICATOR
44, 54 CURRENT DETECTOR
45 VOLTAGE DETECTOR
46 PHASE COMPARATOR
47 RESISTOR
55 RESONANT FREQUENCY OPERATION UNIT

The invention claimed is:

1. A suction device comprising:
a suction unit having a sidewall adapted for being mounted on an affected part;
a suction pump sucking an external fluid using the suction unit with a suction pressure in accordance with a driving voltage, wherein the suction pump has a piezoelectric element operating upon the application of the driving voltage;
a driving controller repeating a state of applying the driving voltage to the suction pump and a state of stopping the application of the driving voltage;
a detection unit detecting a suction state in the suction unit when the driving controller is in a state of outputting the driving voltage,
wherein the driving controller adjusts the driving voltage in accordance with the state detected by the detection unit,
wherein the detection unit detects a state of the suction pump and detects the suction state in the suction unit based on the detected state of the suction pump, and
wherein the detection unit detects a state of an impedance of the piezoelectric element of the suction pump as the state of the suction pump; and
a storage unit previously storing a correspondence relation between the suction state in the suction unit and the state of the suction pump,
wherein the detection unit detects the suction state in the suction unit with reference to the storage unit.

2. The suction device according to claim 1,
wherein the detection unit detects an amplitude of an electric current flowing through the piezoelectric element as the state of the impedance of the piezoelectric element.

3. The suction device according to claim 1,
wherein the detection unit detects a phase difference between an electric current flowing through the piezoelectric element and the driving voltage applied to the piezoelectric element as the state of the impedance of the piezoelectric element.

4. The suction device according to claim 1,
wherein the detection unit detects a resonant frequency of the piezoelectric element as the state of the impedance of the piezoelectric element, and
the driving controller drives the piezoelectric element at the resonant frequency.

5. The suction device according to claim 1, further comprising a notification unit notifying of the state detected by the detection unit.

6. The suction device according to claim 1,
wherein the sidewall of the suction unit has a shape of being inserted into a nasal cavity.

7. The suction device according to claim 2, further comprising a notification unit notifying of the state detected by the detection unit.

8. The suction device according to claim 3, further comprising a notification unit notifying of the state detected by the detection unit.

9. The suction device according to claim 4, further comprising a notification unit notifying of the state detected by the detection unit.

10. The suction device according to claim 1,
wherein the sidewall of the suction unit has a shape of being inserted into a nasal cavity.

* * * * *

UNITED STATES PATENT AND TRADEMARK OFFICE
CERTIFICATE OF CORRECTION

PATENT NO. : 10,398,809 B2  
APPLICATION NO. : 15/402733  
DATED : September 3, 2019  
INVENTOR(S) : Nobuhira Tanaka Page 1 of 1

It is certified that error appears in the above-identified patent and that said Letters Patent is hereby corrected as shown below:

In the Specification

Column 8, Line 4, "Time is" should read -- Time ts --

Column 8, Line 8, "Time to" should read -- Time te --

Signed and Sealed this  
Twenty-ninth Day of September, 2020

Andrei Iancu  
*Director of the United States Patent and Trademark Office*